United States Patent [19]
Ichikawa et al.

[11] Patent Number: 5,324,730
[45] Date of Patent: Jun. 28, 1994

[54] PHENOXYPHOSPHORYLOXYMETHYL CYCLOBUTYL PURINES

[75] Inventors: Yuh-ichiro Ichikawa; Hiroshi Akaba, both of Tokyo; Yuka Sugawara, Kashiwa; Hideo Sugimura, Tokyo; Kazuhisa Narita, Ageo; Akira Shiozawa, Omiya; Kouwa Yamashita; Sayuri Kato, both of Urawa; Yukihiro Nishiyama, Aichi; Kenichi Matsubara, Suita; Takemitsu Nagahata, Toyonaka, all of Japan

[73] Assignee: Nippon Kayaku Kabushiki Kaisha, Tokyo, Japan

[21] Appl. No.: 704,085
[22] Filed: May 22, 1991

[30] Foreign Application Priority Data

May 24, 1990 [JP] Japan .................................. 2-132686

[51] Int. Cl.$^5$ ..................... A61K 31/52; C07D 473/18; C07D 473/32; C07F 9/09
[52] U.S. Cl. ......................... 514/262; 514/266; 544/243; 544/244; 544/265; 544/276; 544/277
[58] Field of Search ............... 544/244, 265, 277, 276, 544/243; 514/262, 266

[56] References Cited

U.S. PATENT DOCUMENTS

| | | | |
|---|---|---|---|
| 4,816,447 | 3/1989 | Ashton et al. | 544/244 |
| 4,845,215 | 7/1989 | Shimada | 544/265 |
| 4,892,876 | 1/1990 | Hoshino | 514/265 |
| 4,960,910 | 10/1990 | Kato | 549/510 |
| 4,992,368 | 2/1991 | Saito | 435/88 |
| 5,028,598 | 7/1991 | Kurabayashi | 514/81 |
| 5,041,447 | 8/1991 | Saito | 514/262 |

FOREIGN PATENT DOCUMENTS

| | | |
|---|---|---|
| 0291917 | 11/1988 | European Pat. Off. . |
| 0322854 | 7/1989 | European Pat. Off. . |
| 0334250 | 9/1989 | European Pat. Off. . |
| 0366059 | 2/1990 | European Pat. Off. . |
| 0358154 | 3/1990 | European Pat. Off. . |
| 3-504728 | 10/1991 | Japan . |

OTHER PUBLICATIONS

Antiviral Research, vol. 13, No. 1, Jan. 1990, pp. 41–52 Elsevier Science Publishers B.V. (Biomedical Division); A. K. Field et al.
Tetrahedron Letters, 29, 4739–4742, 1988.
Kurabayashi et al., "Preparation of novel oxetane, etc." CA115:136655t (1991).
Antimicrobial Agents and Ghemotherapy, May 1989, pp. 773–775.
The Journal of Antibiotics, vol. 17, No. 4, 644–646, 1989.
XXIX Interscience Conference on Antimicrobial Agents and Chemotherapy Sep. 17–20, 1989, "Biomedical Activity of the New Antiviral SO 32,829".
XXIX Interscience Conference on Antimicrobial Agents and Chemotherapy Sep. 17–20, 1989, "In vitro Activity of SQ-32,829, A New Nucleoside-Analog Antiviral Agent," 1989.
XXIX Interscience Conference on Antimicrobial Agents and Chemotherapy Sep. 17–20, 1989, "Efficacy of SQ 33,054 [(±)-BHCG] in Herpes Virus Infections in Mice", 1989.

*Primary Examiner*—Mukund J. Shah
*Assistant Examiner*—Y. N. Gupta
*Attorney, Agent, or Firm*—Nields & Lemack

[57] ABSTRACT

This invention relates to cyclobutane derivatives represented by the following general formula (1) and physiologically acceptable salts thereof:

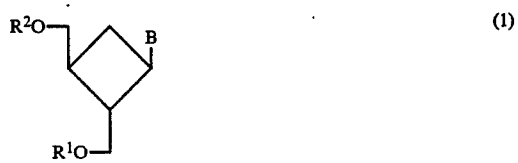

(1)

wherein B represents a nucleic acid base derivative, $R^1$ and $R^2$ independently represent hydrogen atom, dialkylaminoacyl group, 1,4-dihydro-1-methylnicotinoyl group or substituted phosphoric acid group, provided that either one of $R^1$ and $R^2$ is a group other than hydrogen atom.

The compounds of this invention exhibit a high oral absorbability and are metabolized in vivo into the compounds of formula (1a). Accordingly, the compounds of this invention are expectedly useful as antiviral agent.

6 Claims, No Drawings

PHENOXYPHOSPHORYLOXYMETHYL CYCLOBUTYL PURINES

FIELD OF THE INVENTION

This invention relates to cyclobutane derivatives expectedly useful a medical drugs such as antiviral agent, carcinostatic agent and the like.

BACKGROUND OF THE INVENTION

Compounds represented by the following general formula (1a):

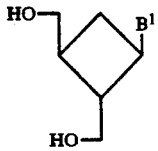

wherein $B^1$ represents a nucleic acid base, exhibit an antiviral activity. Particularly, they exhibit a strong activity against herpes simplex virus 1 and 2 (HSV-1,2), human cytomegalovirus (HCMV), hepatitis B virus (HBV), human immunodeficiency virus (HIV), etc. Further, there are disclosed a variety of analogues of these compounds (EP 0335355-A2, EP 0358154-A2, EP 0366059-A2).

SUMMARY OF THE INVENTION

This invention relates to cyclobutane derivatives represented by the following general formula (1) and physiologically acceptable salts thereof:

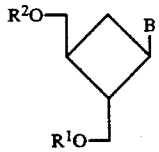

wherein B represents a nucleic acid base derivative and $R^1$ and $R^2$ independently represent hydrogen atom, dialkylaminoacyl group, 1,4-dihydro-1-methylnicotinoyl group or substituted phosphoric acid group, provided that either one of $R^1$ and $R^2$ is a group other than hydrogen atom.

The compounds of this invention have a high oral absorbability and are metabolized in vivo into the above-mentioned compounds (1a). Accordingly, the compounds of this invention are expectedly useful as antiviral agent.

In general formula (1), examples of the nucleic acid base derivative B include purine bases, pyrimidine bases and those bases protected by a protecting group. As examples of said purine base, the followings can be referred to:

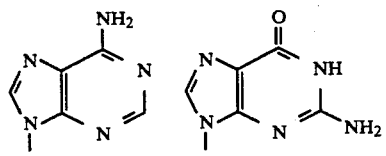

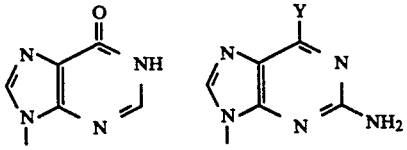

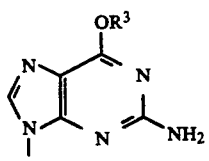

wherein Y represents hydrogen, amino group or halogen such as chlorine, bromine, fluorine and the like, and $R^3$ represents $(C_1-C_4)$ alkyl group such as methyl, ethyl, butyl and the like, $(C_1-C_4)$ alkoxy-$(C_1-C_4)$ alkyl group such as methoxyethyl and the like, or phenyl-substituted $(C_1-C_4)$ alkyl group such as benzyl and the like.

As examples of said pyrimidine base, the followings can be referred to:

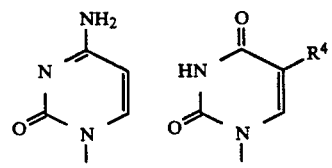

wherein $R^4$ represents hydrogen, $(C_1-C_4)$ alkyl group such as methyl, ethyl, butyl and the like, phenyl-substituted $(C_1-C_4)$ alkyl group such as benzyl and the like, halogenated vinyl group such as 2-bromovinyl, 2-iodovinyl and the like, or halogen such as fluorine, chlorine, bromine and iodine.

In general formula (1), examples of the dialkylaminoacyl group represented by $R^1$ and $R^2$ include di$(C^1-C^4)$alkylamino$(C_1-C_4)$alkylcarbonyl groups such as dimethylaminoacetyl group, diethylaminopropionyl group, dimethylaminobutyryl group and the like, pyrrolidino-propionyl group, and the like. The term "substituted phosphoric acid group" means phosphoric acid groups linked to one or two substituents through intermediation of phosphoric ester bond, and said substituent includes $(C_1-C_{20})$ alkyl groups such as methyl, ethyl, octyl octadecyl and the like, substituted alkyl groups and aryl groups including phenyl group, pyridyl group, halogenophenyl groups such as 2-chlorophenyl, 3-chloro-phenyl, 4-fluorophenyl and the like and $(C_1-C_4)$ alkyl-phenyl groups such as 4-methylphenyl, $(C_1-C_4)$ alkoxy-phenyl group such as 4-methoxyphenyl and the like. As used herein, the term "substituted alkyl group" means straight or branched chain alkyl groups having an aromatic substituent such as phenyl, 3,4-dihydroxyphenyl, pyridyl and the like, an amino substituent such as amino, dimethylamino and the like, a hydroxy substituent, a carboxy substituent, and those substituents into which a protecting group is additionally introduced The preferable group in R2 is phenylphosphoryl group in which the phenyl group is optionally substituted by halogen, $(C_1-C_4)$ alkyl group or $(C_1-C_4)$ alkoxy group.

As said protecting group, all the groups which are generally used as a protecting group can be used without restriction. As said protecting group, ester type protecting groups such as acyl groups (acetyl, benzoyl and the like) and carbamoyl groups (dimethyl-carbamoyl, diphenylcarbamoyl and the like), silyl type protecting groups such as t-butyldimethylsilyl group, t-butyldiphenylsilyl group and the like, ether type protecting groups such as ($C_1$–$C_4$)alkoxy($C_1$–$C_4$)alkyl groups (methoxymethyl and the like), tetrahydropyranyl group and the like, and substituted methyl type protecting groups having one or more substituted or unsubstituted phenyl substituent(s) such as benzyl group, 4-methoxybenzyl group, trityl group and the like, can be referred to.

As for the steric configuration of substituents in general formula (1), compounds wherein substituent B and its adjacent hydroxymethyl group are in a trans relationship and the hydroxymethyl group adjacent to substituent B and the other hydroxymethyl group are in a trans relationship are preferable, and (1R,2R,3S) compounds are more preferable.

Said "physiologically acceptable salts" include alkali metal salts such as sodium salt, potassium salt and the like, alkaline earth metal salts such as calcium salt, magnesium salt and the like, ammonium salt, substituted ammonium salts, salts of mineral acids such as hydrochloric acid, sulfuric acid, nitric acid and the like, and salts of organic acids such as acetic acid, fumaric acid, maleic acid, tartaric acid, methane-sulfonic acid and the like.

Next, concrete examples of the compound represented by general formula (1) will be shown below. Racemic mixtures of the compounds shown hereinunder are also included in the compounds of general formula (1). As for salts, no examples are shown herein.

1. 9-[1R,2R,3S)-2-(ethoxyhydroxyphosphoryl)-oxymethyl-3-hydroxymethyl-1-cyclobutyl]-guanine
2. 9-[(1R,2R,3S)-3-(ethoxyhydroxyphosphoryl)-oxymethyl-2-hydroxymethyl-1-cyclobutyl]-guanine
3. 9-[(1R,2R,3S)-2,3-bis((ethoxyhydroxy-phosphoryl)oxymethyl)-1-cyclobutyl]-guanine
4. 9-[(1R,2R,3S)-3-hydroxymethyl-2-(hydroxy(n-propoxy)phosphoryl)oxymethyl-1-cyclobutyl]-guanine
5. 9-[(1R,2R,3S)-2-hydroxymethyl-3-(hydroxy(n-propoxy)phosphoryl)oxymethyl-1-cyclobutyl]-guanine
6. 9-[(1R,2R,3S)-2,3-bis((hydroxy(n-propoxy)-phosphoryl)oxymethyl)-1-cyclobutyl]-guanine
7. 9-[(1R,2R,3S)-3-hydroxymethyl-2-(hydroxy(n-octyloxy)phosphoryl)oxymethyl-1-cyclobutyl]-guanine
8. 9-[(1R,2R,3S)-2-hydroxymethyl-3-(hydroxy(n-octyloxy)phosphoryl)oxymethyl-1-cyclobutyl]-guanine
9. 9-[(1R,2R,3S)-2,3-bis((hydroxy(n-octyloxy)-phosphoryl)oxymethyl)-1-cyclobutyl]-guanine
10. 9-[(1R,2R,3S)-3-hydroxymethyl-2-(hydroxy(n-octadecyloxy)phosphoryl)oxymethyl-1-cyclobutyl]-guanine
11. 9-[(1R,2R,3S)-2-hydroxymethyl-3-(hydroxy(n-octadecyloxy)phosphoryl)oxymethyl-1 cyclobutyl]-guanine
12. 9-[(1R,2R,3S)-2,3-bis((hydroxy(n-octade-cyloxy)-phosphoryl)oxymethyl)-1-cyclobutyl]-guanine
13. 9-[(1R,2R,3S)-3-hydroxymethyl-2-(hydroxy(phenoxy)phosphoryl)oxymethyl-1-cyclobutyl]-guanine
14. 9-[(1,2R,3S)-2-hydroxymethyl-3-(hydroxy(phenoxy)phosphoryl)oxymethyl-1-cyclobutyl]-guanine
15. 9-[(1R,2R,3S)-2,3-bis((hydroxy(phenoxy)-phosphoryl)oxymethyl)-1-cyclobutyl]-guanine
16. 9-[(1R,2R,3S)-3-hydroxymethyl-2-(hydroxy(phenethyloxy)phosphoryl)oxymethyl-1-cyclobutyl]-guanine
17. 9-[(1R,2R,3S)-2-hydroxymethyl-3-(hydroxy(phenethyloxy)phosphoryl)oxymethyl-1-cyclobutyl]-guanine
18. 9-[(1R,2R,3S)-2,3-bis((hydroxy(phenethyloxy)-phosphoryl)oxymethyl)-1-cyclobutyl]-guanine
19. 9-[(1R,2R,3S)-2-(4-dimethylaminobutyryl)-oxymethyl-3-hydroxymethyl-1-cyclobutyl]-guanine
20. 9-[(1R,2R,3S)-3-(4-dimethylaminobutyryl)-oxymethyl-3-hydroxymethyl-1-cyclobutyl]-guanine
21. 9-[(1R,2R,3S)-2,3-bis((4-dimethylaminobutyryl)oxymethyl-1-cyclobutyl]-guanine
22. 9-[(1R,2R,3S)-2-(1,4-dihydro-1-methyl-nicotinoyl)oxymethyl-3-hydroxymethyl-1-cyclobutyl]-guanine
23. 9-[(1R,2R,3S)-3-(1,4-dihydro-1-methyl-nicotinoyl)oxymethyl-2-hydroxymethyl-1-cyclobutyl]-guanine
24. 9-[(1R,2R,3S)-2,3-bis((1,4-dihydro-1-methyl-nicotinoyl)oxymethyl)-1-cyclobutyl]-guanine
25. 9-[(1R,2R,3S)-3-(ethoxyhydroxyphosphoryl)-oxymethyl-2-hydroxymethyl-1-cyclobutyl]-adenine
26. 9-[(1R,2R,3S)-2-hydroxymethyl-3-(hydroxy(n-propoxy)phosphoryl)oxymethyl-1-cyclobutyl]-adenine
27. 9-[(1R,2R,3S)-2-hydroxymethyl-3-(hydroxy(n-octyloxy)phosphoryl)oxymethyl-1-cyclobutyl]-adenine
28. 9-[(1R,2R,3S)-2-hydroxymethyl-3-(hydroxy(n-octadecyloxy)phosphoryl)oxymethyl-1-cyclobutyl]-adenine
29. 9-[(1R,2R,3S)-2-hydroxymethyl-3-(hydroxy(phenoxy)phosphoryl)oxymethyl-1-cyclobutyl]-adenine
30. 9-[(1R,2R,3S)-2-hydroxymethyl-3-(hydroxy(phenethyloxy)phosphoryl)oxymethyl-1-cyclobutyl]-adenine
31. 9-[(1R,2R,3S)-2-(4-dimethylaminobutyryl)-oxymethyl-3-hydroxymethyl-1-cyclobutyl]-adenine
32. 9-[(1R,2R,3S)-3-(4-dimethylaminobutyryl)-oxymethyl-2-hydroxymethyl-1-cyclobutyl]-adenine
33. 9-[(1R,2R,3S)-2,3-bis((4-dimethylaminobutyryl)oxymethyl)-1-cyclobutyryl]-adenine
34. 9-[(1R,2R,3S)-2-(1,4-dihydro-1-methyl-nicotinoyl)oxymethyl-3-hydroxymethyl-1-cyclobutyl]-adenine
35. 9-[(1R,2R,3S)-3-(1,4-dihydro-1-methyl-nicotinoyl)oxymethyl-2-hydroxymethyl-1-cyclobutyl]-adenine
36. 9-[(1R,2R,3S)-2,3-bis((1,4-dihydro-1-methyl-nicotinoyl)oxymethyl)-1-cyclobutyl]-adenine
37. 2-Amino-9-[(1R,2R,3S)-3-(ethoxyhydroxy-phosphoryl)oxymethyl-2-hydroxymethyl-1-cyclobutyl]-purine
38. 2-Amino-9-[(1R,2R,3S)-2-hydroxymethyl-3-(hydroxy(n-propoxy)-phosphoryl)oxymethyl-1-cyclobutyl]-purine
39. 2-Amino-9-[(1R,2R,3S)-2-hydroxymethyl-3-(hydroxy(n-octyloxy)phosphoryl)oxymethyl-1-cyclobutyl]-purine
40. 2-Amino-9-[(1R,2R,3S)-2-hydroxymethyl-3-hydroxy(n-octadecyloxy)phosphoryl)oxymethyl-1-cyclobutyl]-purine
41. 2-Amino-9-[(1R,2R,3S)-2-hydroxymethyl-3-hydroxy(pheynoxy)phosphoryl)oxymethyl-1-cyclobutyl]-purine 42. 2-Amino-9-[(1R,2R,3S)-2-hydroxymethyl-3-(hydroxy(phenethyloxy)phosphoryl)oxymethyl-1-cyclobutyl]-purine
43. 2-Amino-9-[(1R,2R,3S)-2-(4-dimethylaminobutyryl)oxymethyl-3-hydroxymethyl-1-cyclobutyl]-purine
44. 2-Amino-9-[(1R,2R,3S)-3-(4-dimethylaminobutyryl)oxymethyl-2-hydroxymethyl-1-cyclobutyl]-purine
45. 2-Amino-9-[(1R,2R,3S)-2,3-bis((4-dimethylaminobutyryl)oxymethyl)-1-cyclobutyl]-purine
46. 2-Amino-9-[(1R,2R,3S)-2-(1,4-dihydro-1-methylnicotinoyl)oxymethyl-3-hydroxymethyl-1cyclobutyl]-purine
47. 2-Amino-9-[(1R,2R,3S)-3-(1,4-dihydro-1-methylnicotinoyl)oxymethyl-3-hydroxymethyl-1-cyclobutyl]-purine
48. 2-Amino-9-[(1R,2R,3S)-2,3-bis((1,4-dihydro-1-methylnicotinoyl)oxymethyl-1-cyclobutyl]-purine
49. 9-[(1R,2R,3S)-3-hydroxymethyl-2-(hydroxy(2-chlorophenoxy)phosphoryl)oxymethyl-1-cyclobutyl]-guanine
50. 9-[(1R,2R,3S)-2-hydroxymethyl-3-(hydroxy(2-chlorophenoxy)phosphoryl)oxymethyl-1-cyclobutyl]-guanine
51. 9-[(1R,2R,3S)-2,3-bis((hydroxy(2-chloro-phenoxy)phosphoryl)oxymethyl)-1-cyclobutyl]-guanine
52. 9-[(1R,2R,3S)-3-hydroxymethyl-2-(hydroxy(3-chlorophenoxy)phosphoryl)oxymethyl-1-cyclobutyl]-guanine
53. 9-[(1R,2R,3S)-2-hydroxymethyl-3-hydroxy(3-chlorophenoxy)phosphoryl)oxymethyl-1-cyclobutyl]-guanine
54. 9-[(1R,2R,3S)-2,3-bis((hydroxy(3-chloro-phenoxy)phosphoryl)oxymethyl)-1-cyclobutyl]-guanine
55. 9-[(1R,2R,3S)-3-hydroxymethyl-2-(hydroxy(4-chlorophenoxy)phosphoryl)oxymethyl-1-cyclobutyl]-guanine
56. 9-[(1R,2R,3S)-2-hydroxymethyl-3-(hydroxy(4-chlorophenoxy)phosphoryl)oxymethyl-1-cyclobutyl]-guanine
57. 9-[(1R,2R,3S)-2,3-bis((hydroxy(4-chloro-phenoxy)phosphoryl)oxymethyl)-1-cyclobutyl]-guanine
58. 9-[(1R,2R,3S)-3-hydroxymethyl-2-(hydroxy(2-fluorophenoxy)phosphoryl)oxymethyl-1-cyclobutyl]-guanine
59. 9-[(1R,2R,3S)-2-hydroxymethyl-3-(hydroxy(2-fluorophenoxy)phosphoryl)oxymethyl-1-cyclobutyl]-guanine
60. 9-[(1R,2R,3S)-2,3-bis((hydroxy(2 fluoro-phenoxy)phosphoryl)oxymethyl)-1-cyclobutyl]-guanine
61. 9-[(1R,2R,3S)-3-hydroxymethyl-2-(hydroxy(3-fluorophenoxy)phosphoryl)oxymethyl-1-cyclobutyl]-guanine
62. 9-[(1R,2R,3S)-2-hydroxymethyl-3-(hydroxy(3-fluorophenoxy)phosphoryl)oxymethyl-1-cyclobutyl]-guanine
63. 9-[(1R,2R,3S)-2,3-bis((hydroxy(3-fluoro-phenoxy)phosphoryl)oxymethyl)-1-cyclobutyl]-guanine
64. 9-[(1R,2R,3S)-3-hydroxymethyl-2-(hydroxy(4-fluorophenoxy)phosphoryl)oxymethyl-1-cyclobutyl]-guanine
65. 9-[(1R,2R,3S)-2-hydroxymethyl-3-(hydroxy(4-fluorophenoxy)phosphoryl)oxymethyl-1-cyclobutyl]-guanine
66. 9-[(1R,2R,3S)-2,3-bis((hydroxy(4-fluoro-phenoxy)phosphoryl)oxymethyl)-1-cyclobutyl]-guanine
67. 9-[(1R,2R,3S)-3-hydroxymethyl-2-(hydroxy(4-methylphenoxy)phosphoryl)oxymethyl-1-cyclobutyl]-guanine
68. 9-[(1R,2R,3S)-2-hydroxymethyl-3-(hydroxy(4-methylphenoxy)phosphoryl)oxymethyl-1-cyclobutyl]-guanine
69. 9-[(1R,2R,3S)-2,3-bis((hydroxy(4-methylphenoxy)phosphoryl)oxymethyl)-1-cyclobutyl]-guanine
70. 9-[(1R,2R,3S)-3-hydroxymethyl-2-(hydroxy(4-methoxyphenoxy)phosphoryl)oxymethyl-1-cyclobutyl]-guanine
71. 9-[(1R,2R,3S)-2-hydroxymethyl-3-(hydroxy(4-methoxyphenoxy)phosphoryl)oxymethyl-1-cyclobutyl]-guanine
72. 9-[(1R,2R,3S)-2,3-bis((hydroxy(4-methoxyphenoxy)phosphoryl)oxymethyl)-1-cyclobutyl]-guanine
73. 9-[(1R,2R,3S)-3-hydroxymethyl-2-(hydroxy(2-chlorophenoxy)phosphoryl)oxymethyl-1-cyclobutyl]-guanine
74. 9-[(1R,2R,3S)-2-hydroxymethyl-3-(hydroxy(2-chlorophenoxy)phosphoryl)oxymethyl-1-cyclobutyl]-adenine
75. 9-[(1R,2R,3S)-2,3-bis((hydroxy(2-chloro-phenoxy)phosphoryl)oxymethyl)-1-cyclobutyl]-adenine
76. 9-[(1R,2R,3S)-3-hydroxymethyl-2-(hydroxy(3-chlorophenoxy)phosphoryl)oxymethyl-1-cyclobutyl]-adenine
77. 9-[(1R,2R,3S)-2-hydroxymethyl-3-(hydroxy(3-chlorophenoxy)phosphoryl)oxymethyl-1-cyclobutyl]-adenine
78. 9-[(1R,2R,3S)-2,3-bis((hydroxy(3-chloro-phenoxy)phosphoryl)oxymethyl)-1 cyclobutyl]-adenine
79. 9-[(1R,2R,3S)-3-hydroxymethyl-2-(hydroxy(4-chlorophenoxy)phosphoryl)oxymethyl-1-cyclobutyl]-adenine
80. 9-[(1R,2R,3S)-2-hydroxymethyl-3-(hydroxy(4-chlorophenoxy)phosphoryl)oxymethyl-1-cyclobutyl]-adenine
81. 9-[(1R,2R,3S)-2,3-bis((hydroxy(4-chloro-phenoxy)phosphoryl)oxymethyl)-1-cyclobutyl]-adenine
82. 9-[(1R,2R,3S)-3-hydroxymethyl-2-(hydroxy(2-fluorophenoxy)phosphoryl)oxymethyl-1-cyclobutyl]-adenine
83. 9-[(1R,2R,3S)-2-hydroxymethyl-3-(hydroxy(2-fluorophenoxy)phosphoryl)oxymethyl-1-cyclobutyl]-adenine
84. 9-[(1R,2R,3S)-2,3-bis((hydroxy(2-fluoro-phenoxy)phosphoryl)oxymethyl)-1-cyclobutyl]-adenine
85. 9-[(1R,2R,3S)-3-hydroxymethyl-2-(hydroxy(3-fluorophenoxy)phosphoryl)oxymethyl-1-cyclobutyl]-adenine
86. 9-[(1R,2R,3S)-2-hydroxymethyl-3-(hydroxy(3-fluorophenoxy)phosphoryl)oxymethyl-1-cyclobutyl]-adenine
87. 9-[(1R,2R,3S)-2,3-bis((hydroxy(3-fluoro-phenoxy)phosphoryl)oxymethyl)-1-cyclobutyl]-adenine
88. 9-[(1R,2R,3S)-3-hydroxymethyl-2-(hydroxy(4-fluorophenoxy)phosphoryl)oxymethyl-1-cyclobutyl]-adenine
89. 9-[(1R,2R,3S)-2-hydroxymethyl-3-(hydroxy(4-fluorophenoxy)phosphoryl)oxymethyl-1-cyclobutyl]-adenine
90. 9-[(1R,2R,3S)-2,3-bis((hydroxy(4-fluoro-phenoxy)phosphoryl)oxymethyl)-1-cyclobutyl]-adenine
91. 9-[(1R,2R,3S)-3-hydroxymethyl-2-(hydroxy(4-methylphenoxy)phosphoryl)oxymethyl-1-cyclobutyl]-adenine 92. 9-[(1R,2R,3S)-2-hydroxymethyl-3-(hydroxy(4-methylphenoxy)phosphoryl)oxymethyl-1-cyclobutyl]-adenine 93. 9-[(1R,2R,3S)-2,3-bis((hydroxy(4-methyl-phenoxy)phosphoryl)oxymethyl)-1-cyclobutyl]-adenine 94. 9-[(1R,2R,3S)-3-hydroxymethyl-2-(hydroxy(4-methoxyphenoxy)phosphoryl)oxymethyl-1-cyclobutyl]-adenine 95. 9-[(1R,2R,3S)-2-hydroxymethyl-3-(hydroxy(4-methoxyphenoxy)phosphoryl)oxymethyl-1-cyclobutyl]-adenine 96. 9-[(1R,2R,3S)-2,3-bis((hydroxy(4-methoxyphenoxy)phosphoryl)oxymethyl)-1-cyclobutyl]-adenine 97. 2-Amino-9-[(1R,2R,3S)-3-hydroxymethyl-2-(hydroxy(2-chlorophenoxy)phosphoryl)oxymethyl-1-cyclobutyl]-purine 98. 2-Amino-9-[(1R,2R,3S)-2-hydroxymethyl-3-(hydroxy(2-chlorophenoxy)phosphoryl)oxymethyl-1-cyclobutyl]-purine 99. 2-Amino-9-[(1R,2R,3S)-2,3-bis((hydroxy(2-chlorophenoxy)phosphoryl)oxymethyl)-1-cyclobutyl]-purine 100. 2-Amino-9-[(1R,2R,3S)-3-hydroxymethyl-2-(hydroxy(3-chlorophenoxy)phosphoryl)oxymethyl-1-cyclobutyl)-purine 101. 2-Amino-9-[(1R,2R,3S)-2-hydroxymethyl-3-(hydroxy(3-chlorophenoxy)phosphoryl)oxymethyl-1-cyclobutyl]-purine 102. 2-Amino-9-[(1R,2R,3S)-2,3-bis((hydroxy(3-chlorophenoxy)phosphoryl)oxymethyl)-1-cyclobutyl]-purine 103. 2-Amino-9-[(1R,2R,3S)-3-hydroxymethyl-2-(hydroxy(4-chlorophenoxy)phosphoryl)oxymethyl-1-cyclobutyl]-purine 104. 2-Amino-9-[(1R,2R,3S)-2-hydroxymethyl-3-(hydroxy(4-chlorophenoxy)phosphoryl)oxymethyl-1-cyclobutyl]-purine 105. 2-Amino-9-[(1R,2R,3S)-2,3-bis((hydroxy(4-chlorophenoxy)phosphoryl)oxymethyl)-1-cyclobutyl]-purine 106. 2-Amino-9-[(1R,2R,3S)-3-hydroxymethyl-2-(hydroxy(2-fluorophenoxy)phosphoryl)oxymethyl-1-cyclobutyl]-purine 107. 2-Amino-9-[(1R,2R,3S)-2-hydroxymethyl-3-(hydroxy(2-fluorophenoxy)phosphoryl)oxymethyl-1-cyclobutyl]-purine 108. 2-Amino-9-[(1R,2R,3S)-2,3-bis((hydroxy(2-fluorophenoxy)phosphoryl)oxymethyl)-1-cyclobutyl]-purine 109. 2-Amino-9-[(1R,2R,3S)-3-hydroxymethyl-2-(hydroxy(3-fluorophenoxy)phosphoryl)oxymethyl-1-cyclobutyl]-purine 110. 2-Amino-9-[(1R,2R,3S)-2-hydroxymethyl-3-hydroxy(3-fluorophenoxy)phosphoryl)oxymethyl-1-cyclobutyl]-purine 111. 2-Amino-9-[(1R,2R,3S)-2,3-bis((hydroxy(3-fluorophenoxy)phosphoryl)oxymethyl)-1-cyclobutyl]-purine 112. 2-Amino-9-[(1R,2R,3S)-3-hydroxymethyl-2-(hydroxy(4-fluorophenoxy)phosphoryl)oxymethyl-1-cyclobutyl]-purine 113. 2-Amino-9-[(1R,2R,3S)-2-hydroxymethyl-3-(hydroxy(4-fluorophenoxy)phosphoryl)oxymethyl-1-cyclobutyl]-purine 114. 2-Amino-9-[(1R,2R,3S)-2,3-bis((hydroxy(4-fluorophenoxy)phosphoryl)oxymethyl)-1-cyclobutyl]-purine 115. 2-Amino-9-[(1R,2R,3S)-3-hydroxymethyl-2-(hydroxy(4-methylphenoxy)phosphoryl)oxymethyl-1-cyclobutyl]-purine 116. 2-Amino-9-[(1R,2R,3S)-2-hydroxymethyl-3-(hydroxy(4-methylphenoxy)phosphoryl)oxymethyl-1-cyclobutyl]-purine 117. 2-Amino-9-[(1R,2R,3S)-2,3-bis((hydroxy(4-methylphenoxy)phosphoryl)oxymethyl)-1-cyclobutyl]-purine 118. 2-Amino-9-[(1R,2R,3S)-3-hydroxymethyl-2-(hydroxy(4-methoxyphenoxy)phosphoryl)oxymethyl-1-cyclobutyl]-purine 119. 2-Amino-9-[(1R,2R,3S)-2-hydroxymethyl-3-(hydroxy(4-methoxyphenoxy)phosphoryl)oxymethyl-1-cyclobutyl]-purine 120. 2-Amino-9-[(1R,2R,3S)-2,3-bis((hydroxy(4-methoxyphenoxy)phosphoryl)oxymethyl)-1-cyclobutyl]-purine The compounds of this invention represented by general formula (1) can be produced, for example, by reacting a compound represented by general formula (2):

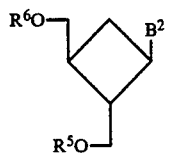

(2)

wherein $R^5$ and $R^6$ represent hydrogen or a protecting group, provided that at least one of $R^5$ and $R^6$ is hydrogen, and $B^2$ represents a nucleic acid base derivative or a protected nucleic acid base derivative, with a compound represented by the following general formula:

R–OH or a reactive derivative thereof wherein R represents alkylaminoacyl group, 1,4-dihydro-1-methylnicotinoyl group or substituted phosphoric acid group, and, when a protecting group is present, subsequently eliminating the protecting group. The compound of the formula R-OH includes a carboxylic acid and phosphoric acid.

For example, as shown in the following reaction scheme (1):

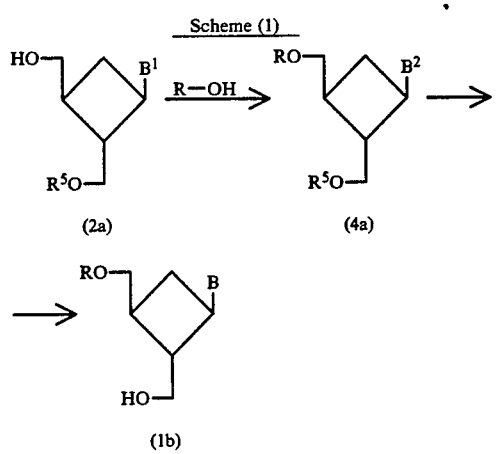

wherein $R^5$ is a protecting group, $B^2$ is as defined in formula (2), R is as defined above and B is as defined in formula (1), a compound represented by general formula (1b) can be obtained by esterifying the hydroxyl group of compound (2a) with a compound represented by the general formula R-OH such as, for example, a phosphate compound and a condensing agent such a dicyclo-hexylcarbodiimide (DCC), water-soluble carbodiimide (WSC) or the like at a temperature of −20° C. to 50° C. in a solvent capable of dissolving compound (2a), preferably a polar solvent such as DMF and the like, and thereafter eliminating the protecting group by an appropriate method such as solvolysis (hydrolysis, ammonoloysis or the like).

In the same manner as above, a compound of the following general formula (1c):

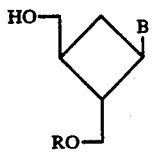
(1c)

wherein B and R are as defined above, can be obtained from a compound of formula (2) wherein $R^6$ is a protecting group and $R^5$ is a hydrogen atom, and a compound of the following general formula (1d):

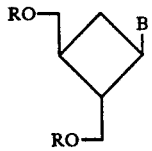
(1d)

wherein B and R are as defined above, can be obtained from a compound of formula (2) wherein $R^5$ and $R^6$ are both hydrogen atom.

When R is a substituted phosphoric acid group, there is no limitation upon the protecting group. However, when R is alkylaminoacyl group or nicotinoyl group, the use of non-(carboxylic acid) type protecting group such as 4,4'-dimethoxytrityl group and the like is more preferable than the use of carboxylic acid type protecting group such as acetyl group.

Next, experiment examples will be presented below to demonstrate the strong antiviral activity and excellent oral absorbability of the compounds of this invention.

EXPERIMENT EXAMPLE 1

Antiviral activity against Herpes simplex 1 virus (HSV-1) which is a DNA virus was tested by the following method.
(Method 1)

Vero cells (originated from kidney cells of African Green Monkey) were cultured in MEM medium to which 10% bovine embryo serum had been added. A cell suspension adjusted to a concentration of 200,000 cells/ml was spread onto 96 wells plate (COSTAR) and cultured for 24 hours so that the cells became confluent. To the medium drawn out was added HSV-1 virus, and it was infected for one hour. Then, the virus fluid was drawn out and cultured for about 72 hours in a fresh medium containing agents. The alive cells were stained with a staining solution containing Neutral Red and absorbance at a wavelength of 546 nm ($A_{546}$) was measured to evaluate the cytopathic effect (CPE).

CPE inhibition (%) was calculated according to the following equation:

$$CPE\ inhibition\ (\%) = 100 \times \left[1 - \frac{A_{546}\ (\text{drug treatment}) - A_{546}\ (\text{virus control})}{A_{546}\ (\text{cell alone}) - A_{546}\ (\text{virus control})}\right]$$

and a quantity of sample enough for 50% inhibition of the CPE due to virus was taken as $IC_{50}$ (μg/ml).

The results are summarized in Table 1.

Experimantal Example 2

Antiviral activity against human cytomegalo-virus (HCMV) which is a DNA virus was tested by the following method.
(Method 2)

Confluent monolayers of human embryonic fibroblasts in plastic dishes (diameter: 35 mm) were infected with 100 to 150 plaque forming units of HCMV. After an 1-hour adsorption period at 37° C., the cultures were overlaid with 2 ml of 0.5% agarose in Eagle's minimum essential medium containing 3% fetal calf serum and various concentrations of drugs. The cultures infected with HCMV were fixed and stained at 9 or 10 days after infection. The second agarose overlay containing appropriate concentrations of drugs was added 5 days after infection. Plaque numbers were counted by using a dissecting microscope at ×20 magnification. The antiviral activities of drugs were expressed in terms of median effective concentrations ($EC_{50}$) which were defined as the drug concentrations that reduced the number of plaques to 50%. The results are summarized in Table 1.

Experimantal Example 3

Antiviral activity against hepatitis B virus (HBV) which is a DNA virus was tested by the following method.
(Method 3)

The test was done by using a cell line, HB611, that was established by transfection and continuously produces HBV like particles [Proc. Natl. Acad. Sci. USA, 84, 444–449, 1987]. HB611 cells were maintained in Dulbecco's modified Eagle medium (Gibco) supplemented with 10% fetal bovine serum (Gibco), 100 μg/ml of streptomycin, 100 IU ml of benzyl penicillin (Gibco) and 200 μg/ml of geneticin (Gibco) at 37° C. in 5% $CO_2$-95% air.

The cells were seeded in 24-well plate (Corning) at a density of $3 \times 10^4$ cells/well, using 1.0 ml of the medium. After 2 days of incubation, the medium was replaced with the same medium containing the test compound. The cells were incubated for a further 15 days, during which time the medium containing the drug was exchanged every three days. The cells were then harvested and cellular DNA was prepared [Virology, 169, 213–216, 1989], and digested with restriction enzyme Hind III (Takara Shuzo Co., Ltd.). An aliquot (2-3 μg) was electrophoresed in 1.5% agarose gel, followed by blotting onto a nylon membrane Hybond-N+ according to Southern [J. Mol. Biol., 98, 503–517, 1975]. The filter was hybridized to random primed 32p labeled HBV DNA probe, and washed twice with 2× standard saline citrate containing 0.1% SDS at 65° C. for 30 min. It was then autoradiographed, and the results were analyzed using a densitometric analyzer (Shimadzu, Chromatoscana S930).

To quantitatively evaluate the inhibitory activity of the compounds, we measured the band areas S, D1, D2 (S, D1 and D2 represent intracellular free HBV DNA derived from replicative intermediates) and I (represents chromosomally integrated HBV DNA) by densitometric analyzer, and calculated the inhibition percentage as follows:

$$\text{Inhibition (\%)} = \left[1 - \frac{(S_{drug} + D1_{drug} + D2_{drug})/I_{drug}}{(S_{cont} + D1_{cont} + D2_{cont})/I_{cont}}\right] \times 100$$

The results are summarized in Table 1.
In table 1, antiviral activity is represented by 50% inhibition doses ($ID_{50}$) on HBV DNA synthesis.

TABLE 1

Anti-HSV-1, anti-HCMV, and anti-HBV activities of the compounds of this invention

| Compound No. | $IC_{50}$ (μg/ml) HSV-1 | $EC_{50}$ (μg/ml) HCMV | $ID_{50}$ (μg/ml) HBV |
|---|---|---|---|
| 50 | 1.13 | 1–3 | ca. 0.1 |
| 53 | 1.22 | 1–3 | 0.1–1.0 |
| 56 | 0.699 | 1–3 | 0.1–1.0 |
| 65 | 1.13 | 1–3 | 0.1–1.0 |
| 68 | 1.26 | 0.1–1 | 0.1–1.0 |
| 71 | 0.873 | 0.1–1 | 0.1–1.0 |

Experiment Example 4

Oral absorbability of compounds of this invention were tested according to the following method.
(Method 4)

Male CDF1 mice (6–8 weeks in age) (Japan Charles Liver Co.) were used. Each substance to be tested was dissolved into physiological salt solution, and its 75 μM/kg dosage (0.1–0.5 ml/10 g dosage) was administered orally or intravenously. Ten minutes, thirty minutes, one hour and 3 hours after the administration, blood was taken from 2–3 heads of mice by means of an injection tube previously treated with heparin, and the blood was centrifuged at 3,000 rpm for 10 minutes to obtain a plasma. To 200 μl of the plasma was added 9-[2-hydroxy-3-hydroxymethylcyclobutan-1-yl]-guanine (2 μg/10 μl $H_2$) as an internal standard. After diluting it with 4 ml of water, it was washed with 2 ml of water by the use of Ceppack $C_{18}$ Cartridge (Millipore Waters Co.). It was eluted with 5 ml of methanol, concentrated to dryness, re-dissolved into 200 μl of water, and then subjected to HPLC to measure the concentration of 9-((1R,2R,3S)-2,3-bis(hydroxymethyl)-1cyclobutyl) guanine (Compound 1a, wherein $B^1$=9-guanyl), from which maximum concentration (Cmax), time of maximum concentration (Tmax) and the area under the concentration curve (AUC) were determined.
(Conditions of HPLC)
Column: Cosmosil 5C18-P (Nacalai Tesque, 250 mm×4.6 mm, i.d.)
Solvent: 0.1 M citric acid (pH 4): acetonitrile:methanol=50:2:1
Flow rate: 1 ml/min.
Wavelength: 254 nm The results of this experiment are summarized in Table 2.

TABLE 2

Concentration of Compound 1a ($B^1$ = 9-guanyl) in plasma after administration of compounds of this invention

| Compound No. | Intravenous injection | | | Oral administration | | |
|---|---|---|---|---|---|---|
| | Cmax (μg/ml) | Tmax | AUC (μg · hr/ml) | Cmax (μg/ml) | Tmax | AUC (μg · hr/ml) |
| 13 | 4.607 | 10' | 2.962 | 1.683 | 30' | 1.122 |
| 14 | 9.485 | 10' | 5.076 | 2.460 | 30' | 2.262 |
| 50 | 5.912 | 10' | 3.177 | 1.057 | 30' | 1.526 |
| 53 | 5.208 | 10' | 3.228 | 0.760 | 30' | 1.405 |
| 56 | 5.167 | 10' | 3.167 | 0.928 | 10' | 1.762 |
| 65 | 6.332 | 10' | 6.373 | 1.345 | 30' | 1.712 |
| 68 | 6.552 | 10' | 4.116 | 1.358 | 30' | 1.754 |
| 71 | 6.700 | 10' | 4.393 | 1.355 | 10' | 1.678 |

As shown above, the compounds of the present invention change by metabolism in living body to the compound 1a ($B^1$=9-guanyl), which is expected to be useful against many viral deseases, described in EP0358154 A2.

Since the compounds of this invention represented by general formula (1) have a strong antiviral activity and a high oral absorbability and a high solubility in water, they are expected to be useful against many viral diseases such as herpes labialis, herpes genitalis, herpes zoster, and infections of herpes simplex virus 1 and 2 (HSV-1, -2), varicella zoster virus (VZV), cytomegalo virus (CMV) and Ebsteinbar virus (EBV), as well as against viral hepatitis, viral diseases of the respiratory organs, viral diseases of the digestive organs, AIDS, ATL and the like. Further they are expectedly useful as an anticancer agent, too.

In putting the compounds of this invention which have been obtained in the above-mentioned manner to use as an antiviral agent or an anticancer agent for mammal, they can be administered orally, intravenously or percutaneously. Its dose is usually 0.1–500 mg/kg/day, though it may vary depending on the symptoms and age of patient and method of administration. The compounds of this invention are administered in the form of a preparation produced by mixing them with an appropriate vehicle. As the form of the preparation, tablet, granule, fine granule, powder, capsule, injection, cream, suppository and the like can be adopted. Content of the compound of this invention in such preparations is about 0.1 to 99%.

Next, production of the compounds of this invention will be illustrated more concretely by way of the following examples.

Example 1

Production of 9-[(1R,2R,3S)-3-(ethoxyhydroxy-phosphoryl)oxymethyl-2-hydroxymethyl-1-cyclobutyl]-guanine (Compound No. 2)

Under a stream of argon gas, 9-[(1R,2R,3S)-2-acetoxymethyl-3-hydroxymethyl-1-cyclobutyl]-guanine (57.4 mg, 0.19 mmole) and ethyl dihydrogen phosphate (0.4 mmole) are dissolved into pyridine (2 ml), and the pyridine is distilled off under reduced pressure. The residue is dissolved into pyridine (2 ml), dicyclohexyl-carbodiimide (DCC) (248 mg, 1.2 mmoles) is added, and the mixture is stirred at room temperature for 2 days. Water (2 ml) is added to the reaction mixture and stirred for one hour, after which volatile substances are distilled off under reduced pressure. After adding an additional quantity of water and distilling off volatile substances under reduced pressure, water (4 ml) is added and the mixture is heated at 100° C. for one hour. After cooling it, concentrated aqueous ammonia (2 ml) is added and stirred overnight. Solvent is distilled off from the reaction mixture under reduced pressure, water is added to the residue, and insoluble matter is filtered off. The filtrate is purified by DEAE Sephadex column chromatography (water 0.5M NaCl) and de-salted by means of a de-salting apparatus (Microacylizer G-1, mfd. by Asahi Kasei Kogyo) to obtain sodium salt of 9-[(1R,2R,3S)-3-(ethoxyhydroxyphos-phoryl)oxymethyl-2-hydroxymethyl-1-cyclobutyl]-guanine (79 mg).

NMR (200 MHzFT, $D_2O$) δ: 1.18 (3H, dt, J=0.73, 7.1 Hz), 2.12–2.38 (2H, m), 2.53 (1H, m), 2.79 (1H, m), 3.67 (2H, d, J=5.9 Hz), 3.79–3.94 (4H, m), 4.46 (1H, m), 7.92 (1H, s).

HRMS (FAB): Calcd for $[C_{13}H_{19}N_5O_6PNa+H]+$; 396.1049. Found; 396.1054

Example 2

Production of 9-[(1R,2R,3S)-2-(ethoxyhydroxy-phosphoryl)-oxymethyl-3-hydroxymethyl-1-cyclobutyl]-guanine (Compound No. 1)

The reaction and after treatment of Example 1 are repeated, except that the 9-[(1R,2R,3S)-2-acetoxymethyl-3-hydroxymethyl-1-cyclobutyl]-guanine is replaced with 9-[(1R,2R,3S)-3-acetoxymethyl-2-hydroxymethyl-1-cyclobutyl]-guanine, to obtain 9-[(1R,2R,3S)-2-(ethoxyhydroxyphosphoryl)-oxymethyl-3-hydroxymethyl-1-cyclobutyl]-guanine (quantitative yield).

NMR (200 MHzFT, $D_2O$) δ: 1.01 (3H, dt, J=0.74, 7.1 Hz), 2.06 (1H, m), 2.24 (1H, m), 2.55 (1H, m), 2.85 (1H, m), 3.58–3.74 (4H, m), 3.92 (2H, t, J=5.8 Hz), 4.55 (1H, m), 7.92 (1H, s).

HRMS (FAB): Calcd for $[C_{13}H_{19}N_5O_6PNa+H]+$; 396.1049. Found; 396.1036.

Example 3

Production of 9-[(1R,2R,3S)-2,3-bis((ethoxyhydroxy-phosphoryl)oxymethyl)-1-cyclobutyl]-guanine (Compound No. 3)

The reaction and after treatment of Example 1 are repeated, except that the 9-[(1R,2R,3S)-2-acetoxymethyl-3-hydroxymethyl-1-cyclobutyl]-guanine is replaced with 9-[(1R,2R,3S)-2,3-bis(hydroxymethyl)-1-cyclobutyl]-guanine and ethyl dihydrogen phosphite is used in an amount of 5 equivalents and DCC is used in an amount of 10 equivalents. Thus, 9-[(1R,2R,3S)-2,3-bis((ethoxyhydroxyphosphoryl)oxymethyl)-1-cyclobutyl]-guanine (17%) is obtained.

NMR (200 MHzFT, $D_2O$) δ: 1.04 (3H, dt, J=0.74, 7.0 Hz), 1.18 (3H, dt, J=0.73, 7.1 Hz), 2.25 (1H, m), 2.35 (1H, m), 2.53 (1H, m), 3.00 (1H, m), 3.70 (2H, quint, J=7.1 Hz), 3.79–4.00 (6H, m), 4.59 (1H, m), 7.98 (1H, s).

HRMS (FAB): Calcd for $[C_{15}H_{23}N_5O_9P_2Na_2+H]+$; 526.0845. Found; 526.0869.

Example 4

The following compounds are obtained by repeating the reaction and after treatment of Examples 1–3, except the reacted reagents are altered.

9-[(1R,2R,3S)-3-hydroxymethyl-2-(hydroxy(n-octyloxy)phosphoryl)oxymethyl-1-cyclobutyl]-guanine (Compound No. 7)

NMR (200 MHzFT, DMSO-$d_6$) δ: 0.83 (3H, diff. t, J=6.4 Hz), 1.05–1.33 (10H, m), 1.33–1.55 (2H, m), 2.03 (1H, m), 2.19 (1H, m), 2.33 (1H, m), 2.84 (1H, m), 3.30–3.85 (6H, overlapped with other peak), 4.49 (1H, apparent q, J=8.4 Hz), 4.97 (1H, brs), 6.94 (2H, brs), 7.83 (1H, s). 9-[(1R,2R,3S)-2-hydroxymethyl-3-(hydroxy(n-octyloxy)phosphoryl)oxymethyl-1-cyclobutyl]-guanine (Compound No. 8)

NMR (200 MHzFT, DMSO-$d_6$) δ: 0.84 (3H, diff, t, J=6.6 Hz), 1.06–1.37 (10H, m), 1.37–1.605 (2H, m), 2.05–2.60 (3H, m), 2.90 (1H, m), 3.30–3.90 (6H, overlapped with other peak), 4.20 (1H, brs), 4.41 (1H, apparent q, J=8.4 Hz), 6.83 (2H, brs), 7.78 (1H, s). 9-[(1R,2R,3S)-2-hydroxymethyl-3-(hydroxy(n-octadecyloxy)phosphoryl)oxymethyl-1-cyclobutyl]-guanine (Compound No. 11)

NMR (200 MHzFT, DMSO-$d_6$) δ: 0.85 (3H, diff, t), 1.10–1.40 (30H, m), 1.45–1.67 (2H, m), 2.10–2.65 (3H, m), 2.84 (1H, m), 3.34–4.06 (6H, overlapped with other peak), 4.49 (1H, apparent q, J=8.4 Hz), 6.42 (2H, brs), 7.84 (1H, s), 10.54 (1H, brs).

9-[(1R,2R,3S)-3-hydroxymethyl-2-(hydroxy(phenoxy)phosphoryl)oxymethyl-1-cyclobutyl]-guanine (Compound No. 13)

NMR (200 MHzFT, DMSO-$d_6$) δ: 1.92–2.24 (2H, m), 2.31 (1H, m), 2.85 (1H, m), 3.40–3.55 (2H, overlapped with other peak), 3.68–3.95 (2H, m), 4.46 (1H, apparent q, J=8.4 Hz), 4.82 (1H, brt, J=4.7 Hz), 6.71 (2H, brs), 7.05–7.24 (5H, m), 7.80 (1H, s), 10.92 (1H, brs). 9-[(1R,2R,3S)-3-hydroxymethyl-2-(hydroxy-(phenethyloxy)phosphoryl)oxymethyl-1-cyclobutyl]-guanine (Compound No. 16)

NMR (200 MHzFT, DMSO-$d_6$) δ: 2.01 (1H, m), 2.16 (1H, m), 2.33 (1H, m), 2.71–2.88 (3H, m), 3.40–3.75 (4H, overlapped with other peak), 3.82 (2H, q J=7.2 Hz), 4.43 (1H, apparent q, J=8.5 Hz), 6.93 (2H, brs), 7.06–7.36 (5H, m), 7.87 (1H, s). 9-[(1R,2R,3S)-2-hydroxymethyl-3-(hydroxy-(phenethyloxy)phosphoryl)oxymethyl-1-cyclobutyl]-guanine (Compound No. 17)

NMR (200 MHzFT, DMSO-$d_6$) δ: 2.04–2.41 (3H, m), 2.73–2.93 (3H, m), 3.33–3.60 (2H, overlapped with other peak), 3.67–3.80 (2H, m), 3.87 (2H, q, J=7.0 Hz), 4.43 (1H, apparent q, J=8.5 Hz), 4.95 (1H, brs), 6.87 (2H, brs), 7.11–7.35 (5H, m), 7.81 (1H, s), 11.13 (1H, brs).

9-[(1R,2R,3S)-2,3-bis((4-dimethylaminobutyryl)oxymethyl)-1-cyclobutyl]-guanine (Compound No. 21)

NMR (200 MHzFT, $D_2O$) δ: 1.62–1.80 (2H, m), 1.88–2.07 (2H, m), 2.11–2.70 (7H, m), 2.76 (6H, s), 2.83 (6H, s), 2.86–3.05 (3H, m), 3.06–3.18 (2H, m), 4.21 (2H, d, J=5.3 Hz), 4.24 (2H, d, J=6.3 Hz), 4.53 (1H, apparent q, J=8.8 Hz), 7.94 (1H, s).

Example 5

Production of 9-[(1R,2R,3S)-2-hydroxymethyl-3-(hydroxy-(2-chlorophenoxy)phosphoryl)oxymethyl-1-cyclobutyl]-guanine (Compound No. 50)

under a steam of argon gas, 9-[(1R,2R,3S)-2-acetoxymethyl-3-hydroxymethyl-1-cyclobutyl]-guanine (153.7 mg, 0.5 mmole) and (2-chlorophenyl) dihydrogen phosphate (219 mg, 1.05 mmoles) are dissolved into pyridine (5 ml), and the pyridine is distilled off under reduced pressure. The residue is dissolved into pyridine (5 ml), dicyclohexylcarbodiimide (DCC) (650 mg, 3.15 mmoles) is added, and the mixture is stirred at room temperature for 16 hours. Water (5 ml) is added to the reaction mixture and stirred for one hour, after which volatile substances are distilled off under reduced pressure. Further, water (10 ml) is added and volatile substances are distilled off under reduced pressure. Then, water (10 ml) is added, the mixture is heated at 100° C. for one hour and cooled, and then concentrated aqueous ammonia (5 ml) is added and the resulting mixture is stirred at room temperature overnight. Solvent is distilled off from the reaction mixture under reduced pressure, water is added to the residue, and the insoluble matter is filtered off. The filtrate is purified by DEAE Sephadex column chromatography (water, 0.5M NaCl) and further purified by HP-20 column chromatography (water, 50% methanol) to obtain sodium salt of 9-[(1R,2R,3S)-2-hydroxymethyl-3-(hydroxy-(2-chlorophenoxy)phosphoryl)oxymethyl-1-cyclobutyl]guanine (181 mg, 76%).

NMR (200 MHzFT, D$_2$O) δ: 2.10 (1H, m), 2.22 (1H, m), 2.42 (1H, m), 2.56 (1H, m), 3.58 (2H, d, J=5.7 Hz), 3.99 (2H, diff t, J=5.1 Hz), 4.31 (1H, apparent q, J=8.4 Hz), 6.92 (1H, t, J=7.7 Hz), 7.12 (1H, dt, J=1.6 Hz, 7.8 Hz), 7.20-7.32 (2H, m), 7.75 (1H, s).

HRMS (FAB): Calcd for [C$_{17}$H$_{19}$ClN$_5$O$_6$P-Na+H]+; 478.0659. Found; 478.0649.

Example 6

The following compounds are obtained by repeating the reaction and after treatment of Example 5, except that the reacted reagents are altered. 9[-(1R,2R,3S)-2-hydroxymethyl-3-(hydroxy(3-chlorophenoxy)phosphoryl)oxymethyl-1-cyclobutyl]-guanine (Compound No. 53) (Yield: 79%)

NMR (200 MHzFT, D$_2$O) δ: 2.00-2.33 (2H, m), 2.42 (1H, m), 2.59 (1H, m), 3.58 (2H, d, J=5.6 Hz), 3.96 (2H, diff. t, J=5.1 Hz), 4.31 (1H, apparent q, J=8.4 Hz), 6.92-7.20 (4H, m), 7.75 (1H, s).

HRMS (FAB): Calcd for [C$_{17}$H$_{19}$ClN$_5$O$_6$P-Na+H]+; 478.0659. Found; 478.0668.

9-[(1R,2R,3S)-2-hydroxymethyl-3-(hydroxy(4-chlorophenoxy)phosphoryl)oxymethyl-1-cyclobutyl]-guanine (Compound No. 56) (Yield: 78%)

NMR (200 MHzFT, D$_2$O) δ: 1.95-2.31 (2H, m), 2.33-2.54 (2H, m), 3.57 (2H, d, J=5.5 Hz), 3.94 (2H, diff. t, J=5.0 Hz), 4.29 (1H, m), 6.97-7.14 (4H, m), 7.75 (1H, s).

HRMS (FAB): Calcd for [C$_{17}$H$_{19}$ClN$_5$O$_6$P-Na+H]+; 478.0659. Found; 478.0625.

9-[(1R,2R,3S)-2-hydroxymethyl-3-(hydroxy(4-fluorophenoxy)phosphoryl)oxymethyl-1-cyclobutyl]-guanine (Compound No. 65) (Yield: 73%)

NMR (200 MHzFT, D$_2$O) δ: 2.02-2.33 (2H, m), 2.37-2.68 (2H, m), 3.57 (2H, d, J=5.8 Hz), 3.96 (2H, diff. t, J=5.2 Hz), 4.33 (1H, apparent q, J=8.5 Hz), 6.90 (2H, diff. t, J=8.8 Hz), 7.00-7.11 (2H, m), 7.78 (1H, s).

HRMS (FAB): Calcd for [C$_{17}$H$_{19}$FN$_5$O$_6$PNa+H]+; 462.0955. Found; 462.0915.

9-[(1R,2R,3S)-2-hydroxymethyl-3-(hydroxy(4-methylphenoxy)phosphoryl)oxymethyl-1-cyclobutyl]-guanine (Compound No. 68) (Yield: 74%)

NMR (200 MHzFT, D$_2$O) δ: 2.06 (3H, s), 1.96-2.30 (2H, m), 2.32-2.53 (2H, m), 3.55 (2H, d, J=5.5 Hz), 3.88-3.97 (2H, m), 4.28 (1H, apparent q, J=8.4 Hz), 6.94 (4H, s), 7.75 (1H, s).

HRMS (FAB): Calcd for [C$_{18}$H$_{22}$N$_5$O$_6$PNa+H]+; 458.1205. Found; 458.1188.

9-[(1R,2R,3S)-2-hydroxymethyl-3-(hydroxy(4-methoxyphenoxy)phosphoryl)oxymethyl-1-cyclobutyl]]guanine (Compound No. 71) (Yield: 85%)

NMR (200 MHzFT, D$_2$O) δ: 1.96-2.32 (2H, m), 2.32-2.52 (2H, m), 3.57 (2H, d, J=5.4 Hz), 3.62 (3H, s), 3.89-3.98 (2H, m), 4.30 (1H, apparent q, J=8.5 Hz), 6.70 (2H, d, J=8.9 Hz), 7.03 (2H, dd, J=1.05, 8.9 Hz), 7.77 (1H, s).

HRMS (FAB): Calcd for [C$_{18}$H$_{22}$N$_5$O$_7$PNa+H]+; 474.1155. Found; 474.1168.

Example 7

Production of 9-[(1R,2R,3S)-3-(4-dimethylaminobutyryl)oxymethyl-2-hydroxymethyl-1cyclobutyl]-guanine (Compound No. 20)

Under a stream of argon gas, N$^2$-(4,4'-dimethoxytrityl)-9-[(1R,2R,3S)-2-(4,4'-dimethoxy-trityl)oxymethyl-3-hydroxymethyl-1-cyclobutyl]-guanine (360 mg, 0.41 mmole), 4-(dimethylamino)-butyric acid hydrochloride (138.7 mg, 0.83 mmole) and 4-(dimethylamino)-pyridine (10.1 mg, 0.08 mmole) are dissolved into DMF (4 ml), and then the DMF is distilled off under reduced pressure. The residue is dissolved into DMF (4 ml). Pyridine (0.17 ml, 2.07 mmoles) and dicyclohexyl-carbodiimide (DCC) (170.8 mg, 0.83 mmole) are added thereto, and the resulting mixture is stirred at room temperature overnight. After adding water (4 ml) to the reaction mixture and stirring the mixture for one hour, ethyl acetate and water are added and insoluble matter is filtered off. The filtrate is extracted with ethyl acetate. The extract layer is washed with water and saturated aqueous solution of sodium chloride and dried over anhydrous sodium sulfate. Then, volatile substances are distilled off under reduced pressure. 80% acetic acid (30 ml) is added to the residue and stirred overnight. After distilling off the volatile substances from the reaction mixture under reduced pressure, water is added and the water is distilled off. Water is added to the residue and the resulting mixture is washed with ether, after which pH value is adjusted to 9. The solution thus obtained is purified by CM Sephadex column chromatography (water, 0.5M NaCl) and then de-salted by the use of a de-salting apparatus (Microacylizer G-1, mfd. by Asahi Kasei Kogyo) to obtain 9-[(1R,2R,3S)-3-(4-dimethylamino-butyryl)oxymethyl-2-hydroxymethyl-1-cyclobutyl]-guanine hydrochloride (52.0 mg, 30.3%).

9-[(1R,2R,3S)-3-(4-dimethylaminobutyryl)oxymethyl-2-hydroxymethyl-1-cyclobutyl]-guanine:

NMR (200 MHzFT, D$_2$O) δ: 1.88-2.07 (2H, m), 2.07-2.83 (4H, m), 2.49 (2H, t, J=7.3 Hz), 2.83 (6H, s), 3.07-3.18 (2H, m), 3.68 (2H, d, J=5.9 Hz), 4.21 (2H, d, J=5.5 Hz), 4.48 (1H, apparent q, J=8.6 Hz), 7.92 (1H, s).

Example 8

Production of 9-[(1R,2R,3S)-2-hydroxymethyl-3-(hydroxy-(phenoxy)phosphoryl)oxymethyl-1-cyclobutyl]-guanine (Compound No. 14)

Under a stream of argon gas, 9-[(1R,2R,3S)-2-acetoxymethyl-3-hydroxymethyl-1-cyclobutyl]-guanine (92.3 mg, 0.3 mmole) and phenyl dihydrogen phosphate (107.9 mg, 0.62 mmole) are dissolved into pyridine (4 ml), and the pyridine is distilled off under reduced pressure. The residue is dissolved into pyridine (4 ml), dicyclohexylcarbodiimide (DCC) (376.7 mg, 1.8 mmoles) is added thereto, and the mixture is stirred at room temperature for 7 days. After adding water (5 ml) to the reaction mixture and stirring it for one hour, volatile substances are distilled off under reduced pressure. Further, water (10 ml) is added and volatile substances are distilled off under reduced pressure, after which water (8 ml) is added. The resulting mixture is heated at 100° C. for one hour, and then cooled. Then, concentrated aqueous ammonia (4 ml) is added and stirred at room temperature overnight. After distilling off the volatile substances from the reaction mixture under reduced pressure, water is added to the residue and insoluble matter is filtered off. The filtrate is purified by DEAE Sephadex column chromatography (water, 0.5M NaCl) and then additionally purified by HP-20 column chromatography (water, 50% methanol) to obtain sodium salt of 9-[(1R,2R,3S)-2-hydroxymethyl-3-(hydroxy(phenoxy)phosphoryl)-oxymethyl-1-cyclobutyl]-guanine (57.7 mg, 43%).

9-[(1R,2R,3S)-2-hydroxymethyl-3-(hydroxy-(phenoxy)-phosphoryl)oxymethyl-1-cyclobutyl]-guanine:

NMR (200 MHzFT, DMSO-d$_6$) δ: 2.05-2.35 (3H, m), 2.81 (1H, m), 3.40-3.55 (2H, overlapped with other peak), 3.81-3.91 (2H, m), 4.41 (1H, apparent q, J=8.2 Hz), 4.92 (1H, brs), 6.87 (2H, brs), 7.09-7.28 (5H, m), 7.75 (1H, s).

Referential Example 1

Production of 9-[(1R,2R,3S)-2-acetoxymethyl-3-hydroxymethyl-1-cyclobutyl]-guanine and 9-[(1R,2R,3S)-3-acetoxymethyl-2-hydroxymethyl-1-cyclobutyl]-guanine Under a stream of argon gas, 9-[(1R,2R,3S)-2,3-bis(-hydroxymethyl)-1-cyclobutyl]-guanine (500 mg, 1.85 mmoles) is dissolved into DMF (10 ml) at 40 to 50° C., and the DMF is distilled off under reduced pressure. The residue is dissolved into DMF (25 ml). Pyridine (0.30 ml, 3.7 mmoles) and acetic anhydride (0.17 ml, 1.85 mmoles) are added, and the mixture is stirred at room temperature for 3 days. After distilling off volatile substances from the reaction mixture under reduced pressure, the product is separated and purified by HP-20 column chromatography (water, 70% methanol) to obtain: 9-[(1R,2R,3S)-2-acetoxymethyl-3hydroxymethyl-1cyclobutyl]-guanine (127 mg, 22%):

NMR (200 MHzFT, CD$_3$OD) δ: 1.96 (3H, s), 2.19 (1H, m), 2.28-2.59 (2H, m), 3.01 (1H, m), 3.68 (2H, d, J=5.3 Hz), 4.15-4.32 (2H, m), 4.59 (1H, apparent q, J=8.8 Hz), 7.86 (1H, s). and 9-[(1R,2R,3S)-3-acetoxymethyl-2-hydroxymethyl-1cyclobutyl]-guanine (150 mg, 26%):

NMR (200 MHzFT, DMSO-d$_6$) δ: 2.03 (3H, s), 2.02-2.50 (3H, m), 2.75 (1H, m), 3.42-3.51 (2H, m), 4.07-4.24 (2H, m), 4.48 (1H, apparent q, J=8.3 Hz), 4.69 (1H, diff. t, J=5.3Hz), 6.40 (2H, brs), 7.89 (1H, s), 10.57 (1H, brs).

Referential Example 2

Production of N$^2$-(4,4'-dimethoxytrityl)-9-[(1R,2R,3S)-2-(4,4'-dimethoxytrityl)oxymethyl-3-hydroxymethyl-1-cyclobutyl]-guanine In an atmosphere of argon gas, 9-(1R,2R,3S)-3-acetoxymethyl-2-hydroxymethyl-1-cyclobutyl-guanine (265 mg, 0.86 mmole) is dissolved into DMF (2 ml) at 40 to 50° C., and the DMF is distilled off under reduced pressure. The residue is dissolved into DMF (5 ml). Triethylamine (0.54 ml, 3.9 mmoles) and 4,4'-dimethoxy-trityl chloride (877 mg, 2.59 mmoles) are added thereto, and the resulting mixture is stirred at room temperature overnight. After distilling off volatile substances from the reaction mixture under reduced pressure, the residue is purified by silica gel column chromatography (methylene chloride:methanol=40:1) to obtain N$^2$-(4,4'-dimethoxytrityl)-9-[(1R,2R,3S)-2-(4,4'-dimethoxytrityl-oxymethyl-3acetoxymethyl-1-cyclobutyl]-guanine (449 mg, 57%).

The N$^2$-(4,4'-dimethoxytrityl)-9-[(1R,2R,3S)-2-(4,4'-dimethoxytrity)oxymethyl-3-acetoxymethyl-1-cyclobutyl]-guanine (447 mg, 0.49 mmole) obtained above is dissolved into a mixture consisting of methanol (5 ml) and methylene chloride (1 ml), potassium carbonate (76 mg, 0.55 mmole) is added under cooling with ice, and the mixture is stirred at room temperature overnight. After adding 0.2M phosphate buffer to the reaction mixture, it is extracted with ethyl acetate. The extract solution is washed with saturated aqueous solution of sodium chloride and dried over anhydrous sodium sulfate, and the solvent is distilled off under reduced pressure. The residue is purified by silica gel column chromatography (methylene chloride:methanol=30:1) to obtain N$^2$-(4,4'-dimethoxytrityl)-9-[(1R,2R,3S)-2-(4,4'-dimethoxytrityl)oxymethyl-3-hydroxymethyl-1-cyclobutyl]-guanine (364 mg, 85%).

NMR (200 MHzFT, CDCl$_3$) δ: 1.97-2.11 (2H, m), 2.27 (1H, m), 3.09 (1H, m), 3.26-3.62 (3H, m), 3.74 (6H, s), 3.76 (6H, s), 4.12 (1H, m), 6.42 (1H, brs), 6.80 (8H, diff. d, J=8.8 Hz), 7.14-7.40 (19H, m), 9.10 (1H, brs).

We claim:

1. A cyclobutane derivative represented by the following general formula (1) and physiological acceptable salts thereof:

wherein B represents a purine base linked at the 9-position, R$^1$ represents hydrogen atom and R$^2$ represents a hydroxy(phenoxy)phosphoryl group optionally submitted by halogen, C$_1$-C$_4$ alkyl group or C$_1$-C$_4$ alkoxy group at the 2-or4-position of the phenoxy group.

2. A cyclobutane derivative according to claim 1, wherein said purine base is guanine.

3. 9-[(1R,2R,3S)-2-(hydroxymethyl-3-(hydroxy-(phenoxy)phosphoryl)oxymethyl-1-cyclobutyl]-guanine.

4. An antiviral agent against a virus comprising a cyclobutane deriviative represented by the following general formula (1) and physiologically acceptable salts thereof:

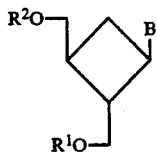

(1)

wherein B represents a purine base linked at the 9-position, R¹ represents hydrogen atom and R² represents a hydroxy(phenoxy)phosphoryl group optionally substituted by halogen, $C_1$–$C_4$ alkyl group or $C_1$–$C_4$ alkoxy group at the 2-or4-position of the phenoxy group.

5. An antiviral agent according to claim 4, wherein B is guanine.

6. An antiviral agent according to claim 4 or 5, wherein the virus is herpes simplex virus, cytomegalo virus or hepatitis B virus.

* * * * *